US00PP09360P

United States Patent [19]

Bradford et al.

[11] Patent Number: Plant 9,360

[45] Date of Patent: Nov. 7, 1995

[54] NECTARINE TREE 'JUNE PEARL'

[76] Inventors: Lowell G. Bradford, 12439 E. Savana Rd.; Norman G. Bradford, 11875 E. Savana Rd., both of Le Grand, Calif. 95333

[21] Appl. No.: 384,129

[22] Filed: Feb. 6, 1995

[51] Int. Cl.[6] ..... A01H 5/00

[52] U.S. Cl. ..... Plt./40.1

[58] Field of Search ..... Plt./40.1

[56] References Cited

U.S. PATENT DOCUMENTS

P.P. 7,050 10/1989 Bradford et al. ..... Plt./41.1

P.P. 8,461 11/1993 Bradford et al. ..... Plt./40.1

*Primary Examiner*—James R. Feyrer

[57] ABSTRACT

The present invention relates to a nectarine tree and more particularly to a new and distinct variety broadly characterized by a large size, vigorous, productive and regular bearing tree. The fruit matures under the ecological conditions described approximately the second week in June, with first picking on Jun. 12, 1994. The fruit is uniformly large in size, non-acidic in flavor, slightly oblong in shape, clingstone in type, firm in texture, and full red in skin color. The variety was a second generation cross of Bradcrim (U.S. Plant Pat. No. 8,461) white flesh nectarine by Diamond Jewel (U.S. Plant No. 7,050) yellow flesh nectarine.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as "June Pearl". The present variety was developed by us in 1989 by growing an open pollinated seed from an unnamed nectarine seedling in a cultivated area of our experimental orchard at Bradford Farms near Le Grand, Calif. in Merced County (San Joaquin Valley). In particular, this unnamed parental nectarine seedling resulted from crossing Bradcrim (U.S. Plant Pat. No. 8,461) white flesh nectarine as the seed parent and Diamond Jewel (U.S. Plant Pat. No. 7,050) yellow flesh nectarine as the pollen parent. Subsequent to origination of the present variety of nectarine tree, we asexually reproduced it by budding and grafting, and such reproduction of plant and fruit characteristics were true to the original plant in all respects.

The fruit produced by the present variety is most similar to its seed grandparent, the Bradcrim (U.S. Plant Pat. No. 8,461), by producing white flesh nectarines that are non-acidic in flavor and virtually free from red texture bleeding, but is distinguished therefrom and an improvement thereon by producing fruit that ripens approximately fifteen days earlier, that is firmer in texture, that is fuller red in skin color, and that is clingstone in type, instead of freestone.

The present variety is similar to its pollen grandparent, Diamond Jewel (U.S. Plant Pat. No. 7,050), by producing large sized, firm, clingstone nectarines that ripen in late June and are nearly full red in skin color, but is very distinguished therefrom by having a large blossom and by producing fruit that is white flesh instead of yellow flesh, and that is non-acidic in flavor instead of acidic.

DRAWING

The accompanying photograph exhibits four whole fruits positioned to display the characteristics of the skin color and form, one fruit divided transversely to the suture plane to reveal the flesh and stone, a stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of shipping ripe on Jun. 16, 1994. All major color code designations are by reference to the Inter-Society Color Council, National Bureau of Standards. Common color names are also used occasionally.

TREE

Size: Large.
Vigor: Vigorous.
Growth: Spreading and dense.
Form: Round topped.
Hardiness: Hardy.
Production: Productive.
Bearing: Regular bearer.
Trunk:
- *Size.*—Medium.
- *Texture.*—Medium.
- *Bark color.*—Grayish brown [61. gy.Br].
- *Lenticels.*—Numerous. Color: Light brown [57. l.Br]. Average size: 3/16" to 5/16" [4.8–7.9 mm.].

Branches:
- *Size.*—Medium.
- *Texture.*—Medium.
- *Color.*—1st year wood topside: Light grayish red [18. l.gy.R]. 1st year wood underside: Brilliant yellow green [116. brill.YG]. Older wood: Grayish brown [61. gy.Br].
- *Lenticels.*—Numerous, small. Color: Moderate yellowish brown [77. m.yBr]. Average size: 1/16" [1.6 mm.].

Leaves:
- *Size.*—Medium. Average length: 5 3/16" [131.8 mm.]. Average width: 1½" [38.1 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Moderate olive green [125.

m.OlG]. Ventral surface: Moderate yellow green [120. m.YG].

*Margin.*—Finely serrate.

*Venation.*—Pinnately net veined. Color: Grayish red [19. gy.R] vein.

*Petiole.*—Average length: 3/8" [9.5 mm.]. Average thickness: 1/16" [1.6 mm.]. Color: Light yellow green [119. l.YG].

*Stipules.*—Numerous. Average length: 1/4" [6.4 mm.].

*Glands.*—Numbers: 2 to 4 per leaf. Position: Alternately positioned on petiole and base of blade. Size: Small. Form: Reniform. Color: Light grayish red [18. l.gy.R].

Flower buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Large.

*Color.*—Moderate pink [5. m.Pk].

FRUIT

Maturity when described: Shipping ripe, Jun. 16, 1994.

Date of first picking: Jun. 12, 1994.

Date of last picking: Jun. 24, 1994.

Size: Uniform, large.

*Average diameter axially.*—2 1/2" [63.5 mm.].

*Average transversely in suture plane.*—2 1/2" [63.5 mm.].

Form: Slightly oblong, slightly variable, slightly unsymmetrical.

*Longitudinal section form.*—Oval.

*Transverse section through diameter.*—Round to elliptical.

Suture: Shallow groove extending from the base to beyond the apex, with slight depression beyond the pistil point, deeper towards the apex.

Ventral surface: Rounded, lipped toward the apex.

Lips: Slightly unequal.

Cavity: Flaring, slightly elongated in suture plane, suture showing on one side.

*Depth.*—3/8" [9.5 mm.].

*Breadth.*—3/8" [9.5 mm.].

Base: Truncate, slightly oblique.

Apex: Most are depressed within the suture, some are protruding, few are mammiform.

Pistil point: Slightly oblique.

Stem: Medium.

*Average length.*—3/8" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—Slight in wet season.

*Color.*—Dark red [16. d.R] over entire surface with slight moderate orange yellow [71. m.OY]. freckling near the apex.

Flesh:

*Color.*—White [263. White] with virtually no bleeding at skin or pit, greenish white [153. gWhite] near the stone, pinkish white [9. pkWhite] near the skin.

*Surface of pit cavity.*—Moderate red [15. m.R] fibers.

*Amygdalin.*—Scarce.

*Juice.*—Abundant, rich.

*Texture.*—Very firm, fine, crisp.

*Fibers.*—Abundant, fine, tender.

*Ripens.*—Evenly, slightly earlier away from the stone.

*Flavor.*—Subacidic to non-acidic and sweet, with 14 to 16 brix.

*Aroma.*—Slight.

*Eating quality.*—Very good.

STONE

Type: Clingstone.

Form: Elliptical.

Base: Straight.

Apex: Acute.

Sides: Equal.

Surface: Horizontally furrowed toward the apex and vertically furrowed toward the base, with only slight pitting.

Ridges: Jagged toward the base.

Color: Light yellowish brown [76. l.yBr].

Pit wall: 3/16" to 1/4" [4.8–6.4 mm.] thick.

Tendency to split: Slight.

Kernel:

*Form.*—Oval.

*Taste.*—Bitter.

*Viable.*—Yes.

*Average width.*—7/16" [11.1 mm.].

*Average length.*—11/16" [17.5 mm.].

*Skin color.*—Moderate reddish brown [43. m.rBr] when dry, pale yellow [89. p.Y] when first removed.

*Pellicle color.*—Grayish yellowish brown [80. gy.yBr].

*Amygdalin.*—Abundant.

USE

Market: Fresh and long distance shipping.

Keeping quality: Very good.

Shipping quality: Very good.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its seed grandparent, the Bradcrim (U.S. Plant Pat. No. 8,461), by producing white flesh nectarines that are non-acidic in flavor and virtually free from red texture bleeding, but is distinguished therefrom and an improvement thereon by producing fruit that ripens approximately fifteen days earlier, that is firmer in texture, that is fuller red in skin color, and that is clingstone in type, instead of freestone.

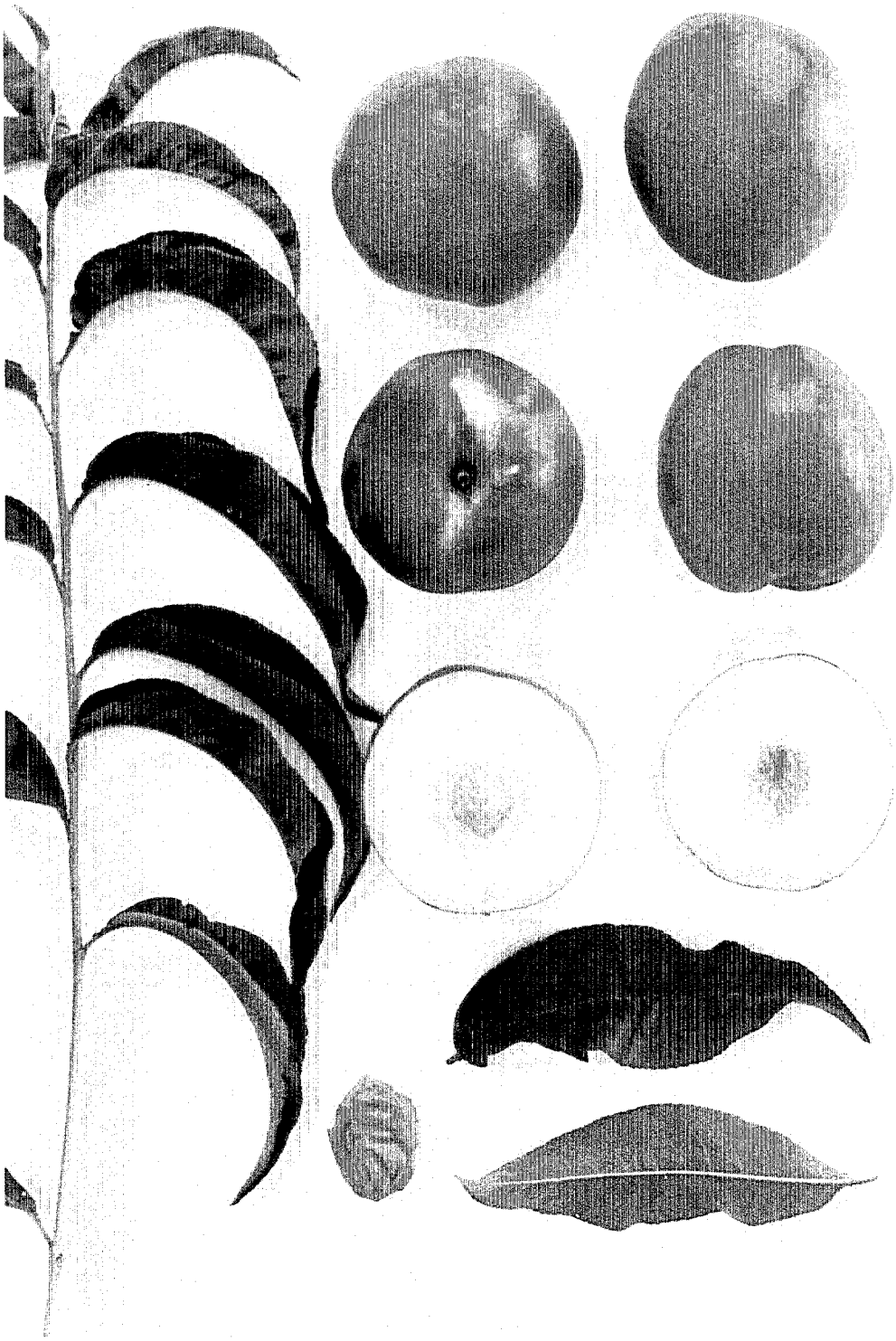

* * * * *